United States Patent [19]
Watano et al.

[11] Patent Number: 5,497,232
[45] Date of Patent: Mar. 5, 1996

[54] APPARTUS AND METHOD FOR MONITORING GRANULAR SIZE AND SHAPE DURING A GRANULATION OR COATING PROCESS

[75] Inventors: Satoru Watano, Osaka; Yoshihiro Itoh, Tokyo; Nobuhito Oda, Tokyo; Teturo Kamata, Tokyo; Noboru Kawakami, Tokyo; Nobuharu Moriya, Osaka, all of Japan

[73] Assignee: Fuji Paudal Co., Ltd., Osaka, Japan

[21] Appl. No.: 300,798

[22] Filed: Sep. 2, 1994

[30] Foreign Application Priority Data

Oct. 26, 1993 [JP] Japan ...................... 5-288833

[51] Int. Cl.$^6$ ................................ G01N 15/02
[52] U.S. Cl. ............................. 356/335; 356/23
[58] Field of Search ................ 356/23, 335, 336

[56] References Cited

U.S. PATENT DOCUMENTS 5,129,268  7/1992  Uesugi et al. .................... 356/335

FOREIGN PATENT DOCUMENTS

| | | |
|---|---|---|
| 54-92389 | 7/1979 | Japan . |
| 57-59143 | 4/1982 | Japan . |
| 58-73730 | 5/1983 | Japan . |
| 59-81535 | 5/1984 | Japan . |
| 60-15541 | 1/1985 | Japan . |
| 63-266339 | 11/1988 | Japan . |
| 3-257347 | 11/1991 | Japan . |
| 4-265142 | 9/1992 | Japan . |
| 5-262590 | 10/1993 | Japan . |
| 5-285363 | 11/1993 | Japan . |
| 2012948 | 8/1979 | United Kingdom . |

*Primary Examiner*—F. L. Evans
*Attorney, Agent, or Firm*—Shefte, Pinckney & Sawyer

[57] ABSTRACT

In the operation of a granulating or coating apparatus wherein a particulate material is processed in a granulation chamber into granules, the material may be photographed during the course of carrying out the granulation process by utilizing a photography probe wherein a bundle of optical fibers are utilized to project a source of stroboscopic illuminating light in the form of a generally flat beam through a portion of the granulating chamber and a photographic camera is focused within the projected light beam along an optical line of sight oriented generally perpendicular to the projected light beam to produce an image of granules within the beam against a relatively dark background. Simultaneously, a stream of gas is directed into the region of the intersection of the projected light beam and the line of camera sight to disperse the charge material to promote photography of individualized particles of the charged material while at the same time preventing accumulation of charge material on the photographic probe.

20 Claims, 11 Drawing Sheets

APPARTUS AND METHOD FOR MONITORING GRANULAR SIZE AND SHAPE DURING A GRANULATION OR COATING PROCESS

BACKGROUND OF THE INVENTION

The present invention relates generally to a method and an apparatus for monitoring the shape and size of particles and granules during granulation and coating processes and relates, more particularly, to such a method and apparatus wherein momentary images of the particles and granules are photographed and analyzed.

For the production of granules, various types of granulation equipment and apparatus are commonly employed, depending upon the purpose and desired quality of end products. Two conventional types of granulators are so-called fluidized bed granulators and tumbling-type granulating apparatus. Granules produced by fluidized bed granulators, for example, are generally of irregular shape and of relatively large size, while granules produced by tumbling-type granulators are relatively spherical in shape.

It is known that the size and shape of such granules depend upon the operational conditions under which granulation takes place and may have relatively large fluctuations making it normally difficult to get consistent granule quality. Thus, depending upon the intended purpose and application of the granules, one specific type of granulator may be selected over another for the production of granules with a specific size and shape.

One of the difficulties encountered in any granulating operation is the selection of the operational parameters for the process and the determination of the point in the process at which operation of the granulator will be stopped. Normally, granule properties are monitored during granulator operation by manual material sampling, but the final properties of the granules are checked only after the granulation process is completed.

Various types of sensing devices to monitor the size and shape of granules during a granulation operation have been developed, but most of them only provide for indirect measurement of granule properties. Specifically, one known conventional monitoring device measures the relative dynamic torque of the main mixing element or rotational element in the granulation chamber as a means of indirectly extrapolating granule size and shape. Another device provides a sensing bar or beam with a strain gauge for insertion into a granulation chamber to measure the degree of deviation of the strain gauge signal due to collision with the granules against the sensor bar as an indication of granule size and shape. A third type of device monitors deviations in power consumption of the main mixing element or rotational element in the granulator as a function of the granule size. Another device measures moisture content of granules as indirectly indicative of the size of granules under process. Therefore, direct measurement or monitoring of individual granule size and shape during a granulating process is increasingly demanded.

Methods for direct measurement of granule size and shape by photographic means are disclosed, for example, in Japanese Patent Application Nos. 54-92389, 59-81535, 63-266339, 60-15541, 57-59143, 58-73730 and 4-265142, the first three of which disclose methods for photographing granules falling from a belt conveyor, with lighting being radiated from a direction opposite or perpendicular to the photographing axis. One problem with these methods is that many granules overlap one another leading to incomplete separation of individual granules in the image processing system and resulting in inaccurate measurement. To overcome this problem, granules should be placed on the belt conveyor so as not to overlap each other. A more fundamental problem is that this method cannot be applied to the photographic analysis of granules in the granulator during processing.

In Japanese Patent Application No. 57-59143, the shape of granules traveling on a belt conveyor is monitored by a so-called linear-sensor camera and granule size is measured by frequency analysis, but this method also cannot be applied to the granules in the granulator during processing. In Japanese Patent Application No. 58-73730, stroboscopic photography is utilized to measure granule size in the mixing and granulation process, but this method suffers the same problem of granule overlapping. Japanese Patent Application No. 4-265142 discloses a method for automated photography during the granulation process in a fluidized bed granulator, by taking a granule sample onto a transparent adhesive tape through which a granule image is obtained. The common problem among these various granule photography methods is that they cannot achieve a substantially separated individual granule image during the granulation and coating process, mainly due to granule overlapping problems.

SUMMARY OF THE INVENTION

It is accordingly an object of the present invention to provide an improved apparatus and method by which granules may be photographed while being processed in a granulating apparatus to achieve a substantially segmented granule image with high visibility, whereby consistent granule size, shape and quality may be achieved.

Briefly summarized, the present invention achieves the foregoing object by providing a granulation or coating apparatus with a device and method for photographing material under process in the granulation chamber of the processing vessel of the apparatus wherein a source of illuminating light is projected through a portion of the granulation chamber and a photographic camera is simultaneously focused within the projected light while a stream of gas is directed in the region of the light projecting means and the camera focusing means to purge process material from accumulating thereon and, at the same time, to disperse the process material in the region to promote photography of individualized particles of the material.

In the preferred embodiment, the present invention provides a unitary photographic probe insertable into the granulation chamber, wherein the light projecting means and the camera focusing means are affixed together as common components of the probe. The illuminating light is preferably produced by a stroboscope and transmitted through the probe by means of a bundle of optical fibers. The stroboscopic projection of light and the focusing of the camera are preferably actuated in timed synchronism with one another.

According to one aspect of the present invention, the illuminating light is projected in the form of a generally flat beam while the camera is focused within the light beam along an optical line of sight oriented generally perpendicular to the projected light beam. The dispersing gas is directed in a first stream generally along the flat projected light beam, preferably by emitting the gas annularly about the light projecting means, and simultaneously in a second stream of gas generally along the optical line of camera sight, preferably discharged annularly about the camera focusing means. The gas in each case may preferably be heated to assist in preventing the process material from accumulating on the photographic probe. A suitable arrangement may be provided for controlling the temperature of the heated gas to maintain it generally constant.

According to another aspect of the present method and apparatus, the photographed images of the process material in the granulation chamber may be utilized for analyzing the state of the granulation process underway in the chamber, particularly with regard to the size and shape of the granules being produced.

Appropriate means may also be provided for sensing the moisture content in the process material within the granulation chamber. In performing the method of the present invention, when the photography of the granules within the chamber indicates that a predetermined mean granule size has been achieved, the moisture content of the granules is measured and, thereafter, is maintained generally constant at the same measured value while the granulating operation is continued until a predetermined granule shape has been achieved or a predetermined distribution of granule sizes has been achieved, whereupon the granulating operation is terminated.

DETAILED DESCRIPTION OF THE PREFERRED EMBODIMENT

Figure 1:
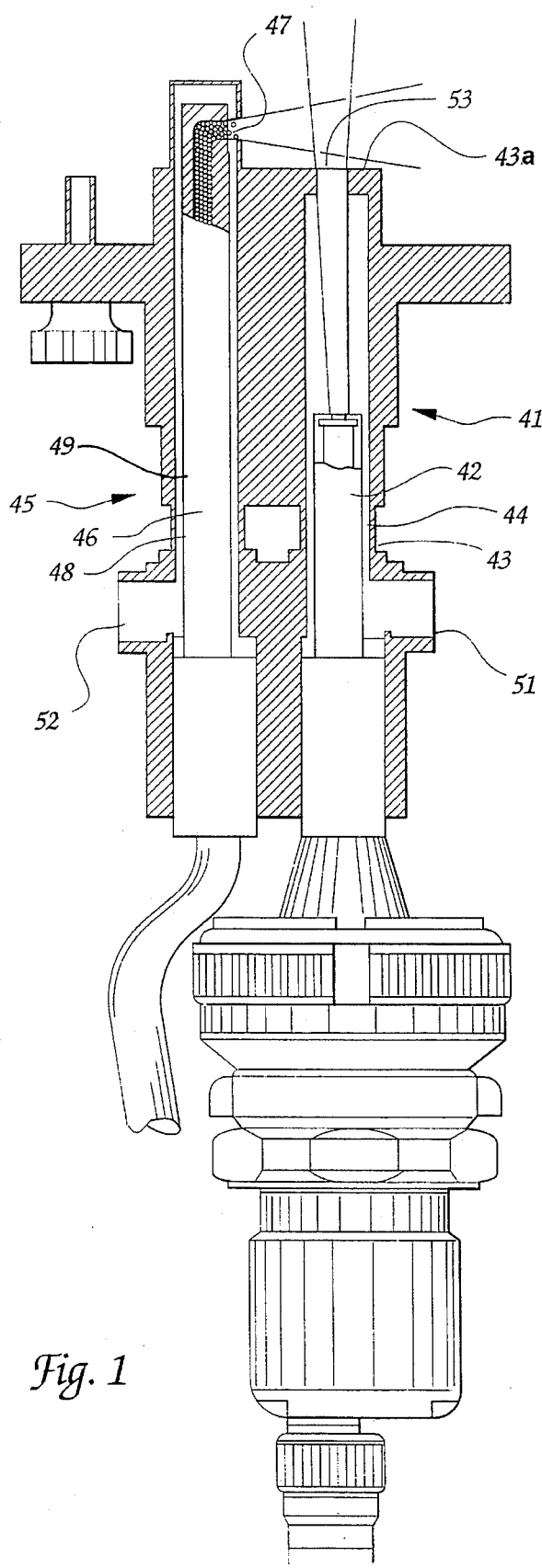
FIG. 1 is a side elevational view, partially in longitudinal cross-section, showing the construction of a stroboscopic photography apparatus according to a preferred embodiment of the present invention.
Figure 1A:
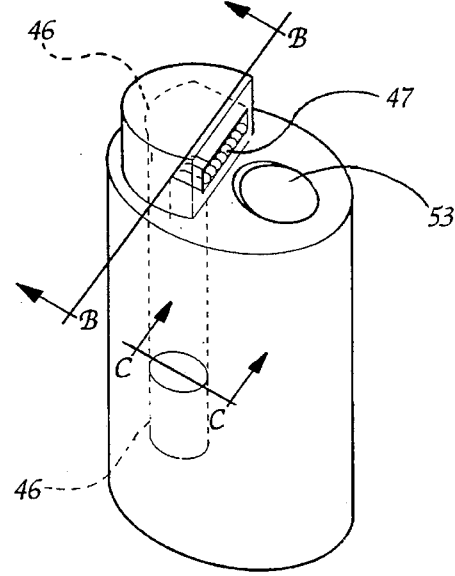
FIG. 1A is a perspective view of the terminal end of the probe of the photography apparatus of FIG. 1.

Referring now to the accompanying drawings and initially to FIG. 2, a granulating apparatus is equipped with an apparatus for stroboscopic photography of the granular contents of the granulating apparatus, basically comprising a photography probe in combination with a still image processing and analysis system, as more fully described below. Basically, the granulation apparatus consists of a granulation and coating chamber 1 within which is disposed a slotted rotating plate 2 and a rotatably mounted agitation element 3. A gas supply conduit 4 opens into the lower end of the granulating apparatus beneath the plate 2 for supplying a fluidizing gas upwardly into the chamber 1 and a spray head 5 is situated above the chamber 1 for downwardly spraying a binding or coating liquid onto charge material in the chamber 1. A product outlet chute 6 opens laterally from the chamber 1 immediately above the plate 2 for discharging granular material upon the completion of a granulating operation. A moisture content detector 7 also opens laterally into the chamber 1 for detecting the moisture content of the granular material therein.

In the operation of the granulating apparatus, powder raw materials are charged into the chamber 1 through a feed chute (not shown) and the powder materials are gradually agglomerated into the form of granules by spraying binding liquid onto the powder material while simultaneously being subjected to fluidized motion by delivery of a gas flow through the gas supply conduit 4 and circulating movement by rotation of the plate 2. By the combined effects of fluidization and plate rotation, the powder materials are forced to move in a circulatory fashion on the rotating plate in the direction indicated by the arrows in FIG. 2.

Figure 2:
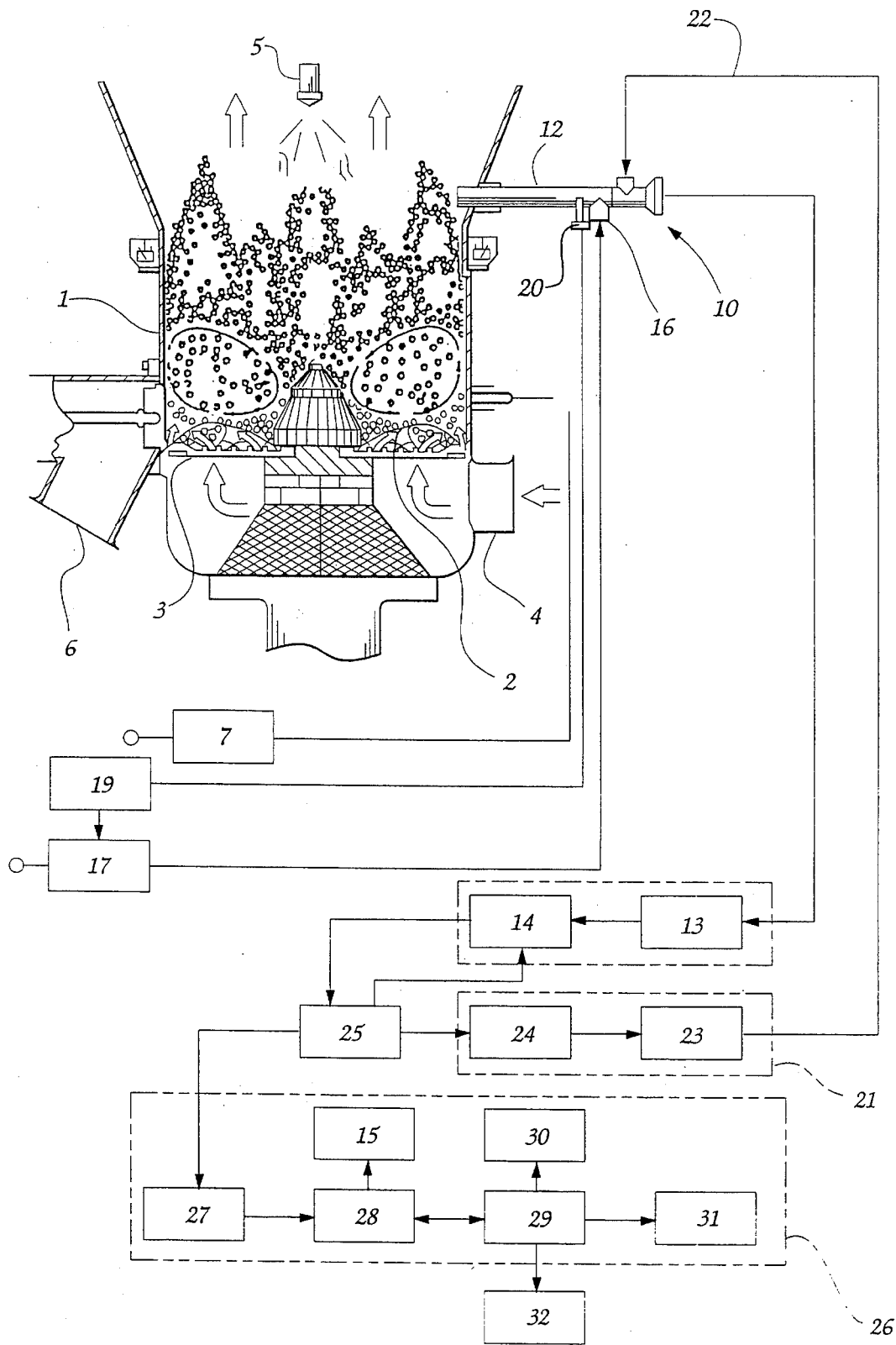
FIG. 2 is a schematic vertical cross-sectional view of an exemplary granulation/coating apparatus in which the photography apparatus of the present invention is employed.
Figure 3:
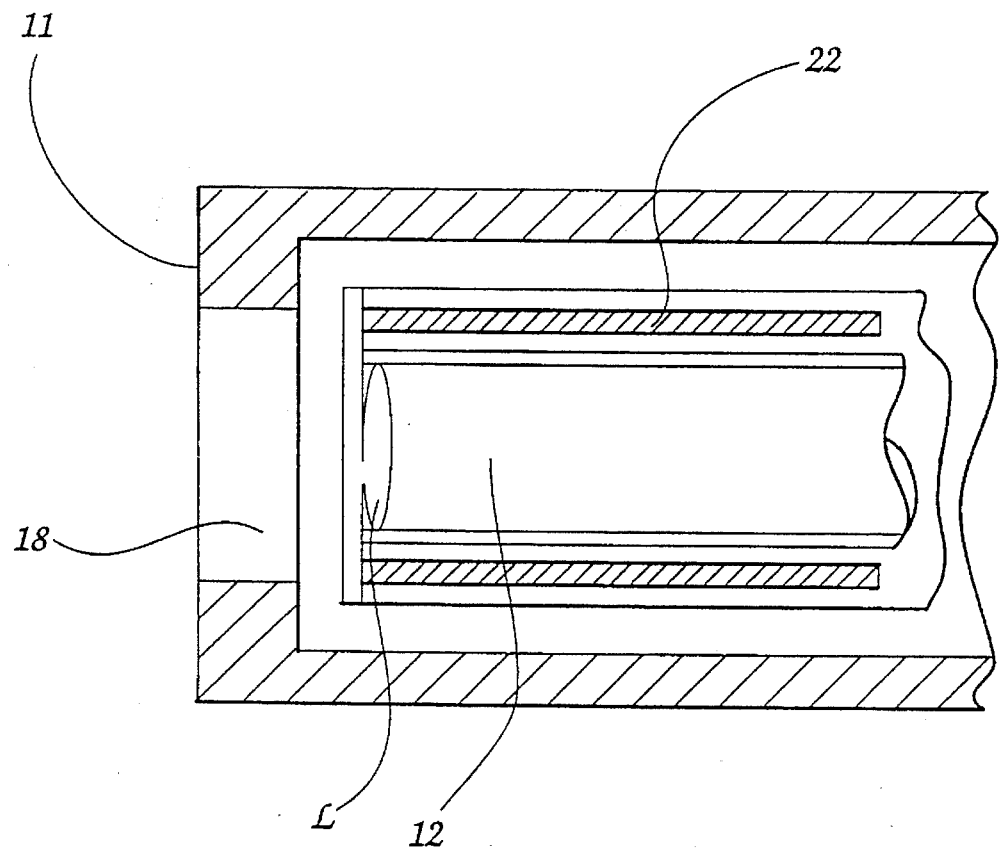
FIG. 3 is an enlarged cross-sectional view of a conventional optical-fiber-scopic probe utilized in the photography apparatus of FIG. 1.

As shown in FIGS. 2 and 3, a photography probe 10 is mounted to the granulating apparatus with a terminal end 11 extending through the wall of the granulation apparatus into the chamber 1. Thus, the terminal end 11 of the probe 10 is disposed to face granules within the chamber 1 while in circulatory action during the granulation process.

An optical fiber scope 12 is disposed in the terminal end of the probe 10 and includes a camera lens L connected to a CCD (charge coupled device) camera 13 of the type used in video tape recorders to convert an image from the lens L into an electrical signal. A visual image of the granules within the chamber 1 converted into an electric signal by the CCD camera 13 is transmitted through a camera control unit (commonly referred to as a CCU) 14 and a still image processor 25 to a particle size and shape analyzer 26. The particle size and shape analyzer 26 consists of a memory unit 27 which may include a videotape recorder, an image analyzer 28, a microprocessor or like computer 29, a printer 30 and one or more displays such as a color CRT (cathode ray tube) 15,31. An input/output interface 32 may be provided for outputting signals for automatic control procedures. With this arrangement of the photography probe 10, the still image processor 25 and the particle size and shape analyzer 26, it is possible to obtain a still image of granules during a granulating operation on the CRT 15 and the printer 30. More importantly, any granulation and/or coating process and the appropriate point in time for terminating the operation can be controlled by the information obtained by these devices.

As shown in FIG. 3, an opening 18 is located at the terminal end 11 of the probe 10 through which a purge gas heated by a gas heater 17 (FIG. 2) may be injected. The temperature of the purge gas is detected by a temperature sensor 20 and is controlled at a certain level by a temperature controller 19 (see FIG. 2).

A high speed stroboscope 21 provides illumination for the camera lens L. Specifically, the stroboscope 21 comprises a stroboscopic light generator 23 which is activated by a signal from a stroboscopic controller 24 actuated in conjunction with the CCU (camera control unit) 14 from the still image processor 25. The light generator 23 transmits light through a bundle of optical fibers 22 which annularly surround the camera lens L within the optical fiber scope 12. In this manner, stroboscopic illumination and photography of granules in the chamber 1 are synchronously carried out.

By equipping the granulating apparatus in FIG. 2 with the photographing system, granule properties such as size and shape may be continuously observed on the color display 15 during a granulating or coating operation. Above all, each still image of granules is analyzed by the high speed processor 26 to obtain detailed real-time information such as granule mean diameter, size distribution, yield and factors relating to granule profile such as aspect ratio and roundness.

Temperature-controlled dry purge gas injected through the head opening 18 in the probe 10 prevents material from sticking to and dimming the lens of the optical and lighting systems to optimize the clarity of the granule image. Additionally, granules disposed within the focal length of the camera 13 are dispersed into individual particles by this purge gas, which promotes an image of the granules separated from one another. Greater separation of the granules in the image reduces the analyzing time and leads to more accurate information.

Figure 11:
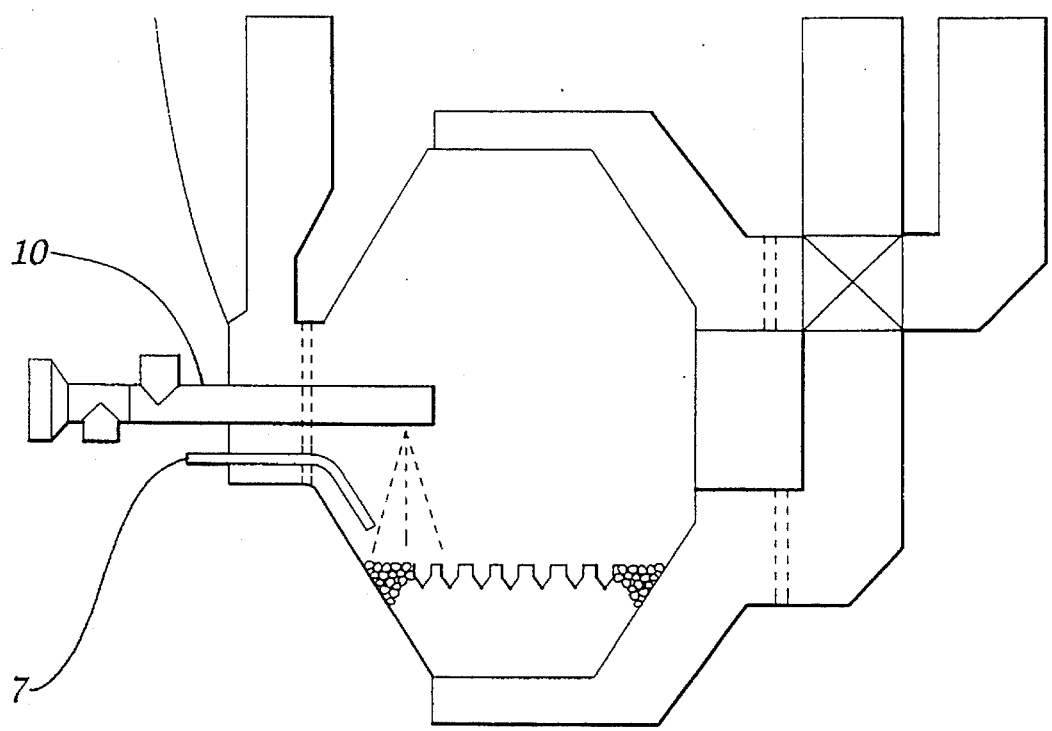
FIG. 11 is a cross-sectional view of a pan-type coating apparatus wherein the photography apparatus of the present invention is employed.

Alternative embodiments of the granulating apparatus of FIG. 2 with differing arrangements and embodiments of the photography probe 10 are shown in FIGS. 5–10. FIG. 11 illustrates an embodiment of the photography probe 10 in a pan-type coating apparatus.

Although this granulating apparatus offers a relatively clear image, some overlapping of the granules still exists which can impair visibility of the contour of the granules in the image. Sophisticated computer software for particle image processing can overcome this problem but is time consuming in operation. An alternative solution is the use of an improved photography probe as shown in FIG. 1. As will be understood, the same image processing system and stroboscopic generating system shown in the block diagram of FIG. 2 can be utilized with the photography probe of FIG. 1.

Figure 1B:
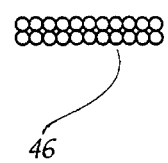
FIG. 1B is a cross-sectional view of the optical fiber bundle within the probe of FIG. 1A taken along line B—B thereof.
Figure 1C:
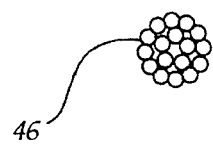
FIG. 1C is a cross-sectional view of the optical fiber bundle within the probe of FIG. 1A taken along line C—C thereof.

The photography probe of FIG. 1 comprises an optical line probe head 41 and a lighting line probe head 45. The optical line probe head 41 functions for photographing granules illuminated by the lighting line probe head 45 and basically consists of a lens barrel 42 secured in an optical line housing 43 with an annular clearance 44 formed between the barrel 42 and the housing 43. In the lighting line probe head 45, an optical fiber bundle 46 is secured within a housing 48 with one terminal end of the fiber bundle 46 facing the stroboscopic lighting generator 23 (FIG. 2) and the other terminal end formed in a linear arrangement at a slit-like opening 47 (FIG. 1B). The terminal end of the lighting line housing 48 extends slightly from a terminal edge 43a of the optical line housing 43. In the lighting line housing 48, an annular clearance is formed between the optical fiber bundle 46 and the housing 48.

Near the bottom of the probe, purge gas inlets 51,52 are provided to which heated gas is supplied. A hot gas at a constant temperature is preferably employed as the purge gas to keep the terminal end of the probe in a dry condition. The purge gas delivered into the inlet 51 is conveyed through the annular clearance 44 around the lens barrel 42 and is ejected from a terminal end opening 53 in the direction of the lens axis, while the purge gas delivered into the inlet 52 is conveyed through the annular clearance 49 around the optical fiber bundle 46 and is ejected from the slit-like opening 47 in a direction substantially normal or perpendicular to the lengthwise axis of the probe.

Instantaneous light produced at the stroboscopic lighting generator is transmitted through the optical fiber bundle 46 and is projected through the slit-like opening 47 in a generally planar beam defined by the opening 47 to illuminate essentially only granules within the planar beam. Advantageously, the stroboscopic light beam crosses over the axial projection of the lens 42 so that, by adjustment of its focal length, the granules within the beam are brightly illuminated in contrast to a dark background, whereby overlapping of the granules in the photographed image is eliminated or greatly minimized.

As aforementioned, the probe is mounted to the granulation apparatus with the terminal end of the probe inserted into the granulation/coating chamber. To avoid the tendency of moistened powder and granules to stick to the end of the probe, the injection of purge gas through the inlets 51,52 keeps the openings 47,53 clean and prevents material sticking problems, promoting in turn a clear image of the granules during operation. Because the axes of the openings 47,53 intersect one another perpendicularly, the gas jets ejected from each opening intersect and the stroboscopic light and the line of photographic imaging projected through each opening also intersect. Thus, the granules or powder adjacent the terminal end opening 53 of the optical line are blown in its axial direction by the gas flow therefrom, while the crossing gas flow from the slit 47 disperses the material into individually separated particles. As a result, the preferred embodiment of the present invention shown in FIG. 1 is enabled to take a photographic image of granules in a substantially individualized condition. Additionally, the stroboscopic lighting emitted from the slit at a right angle to the camera line of sight can create very clear and bright granule images in contrast to a dark or almost black background.

Figure 4:
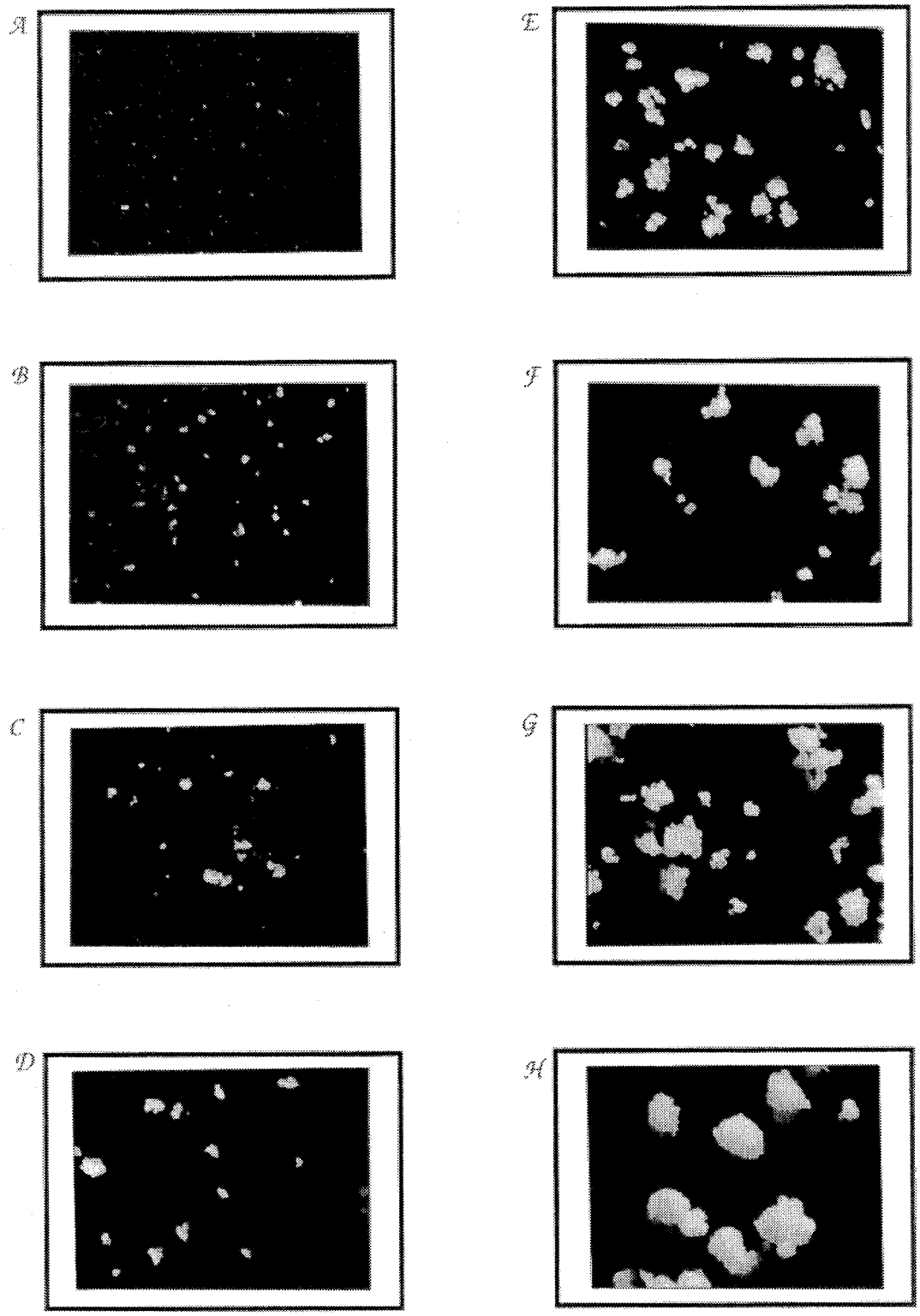
FIGS. 4A–4H are photographs of powder and granular material taken during granulation processes by the photography apparatus of the present invention.
Figure 5:
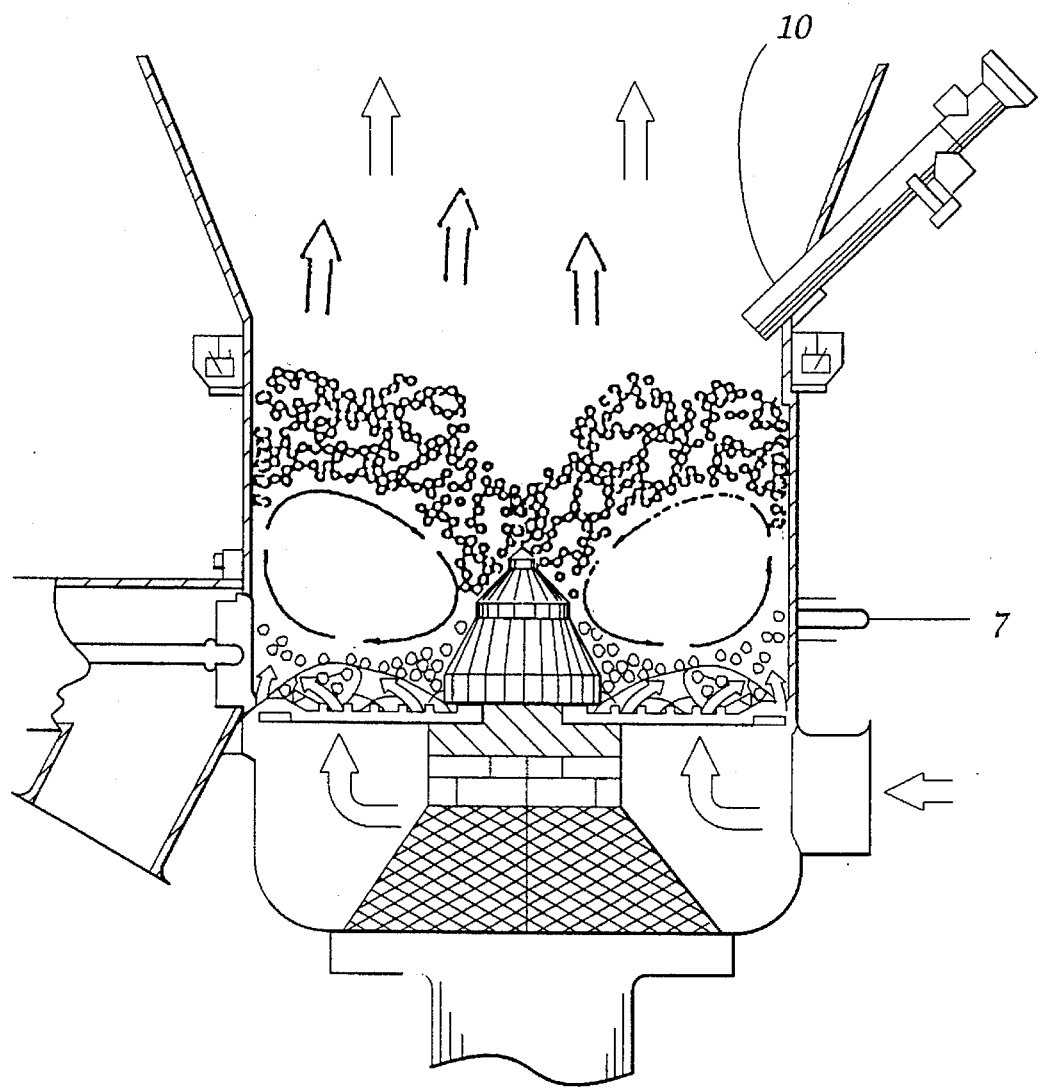
FIG. 5 is a schematic vertical cross-sectional view of a granulation/coating apparatus, similar to FIG. 2, wherein the photography probe of the present apparatus is located in an upper portion of the granulation/coating chamber.
Figure 6:
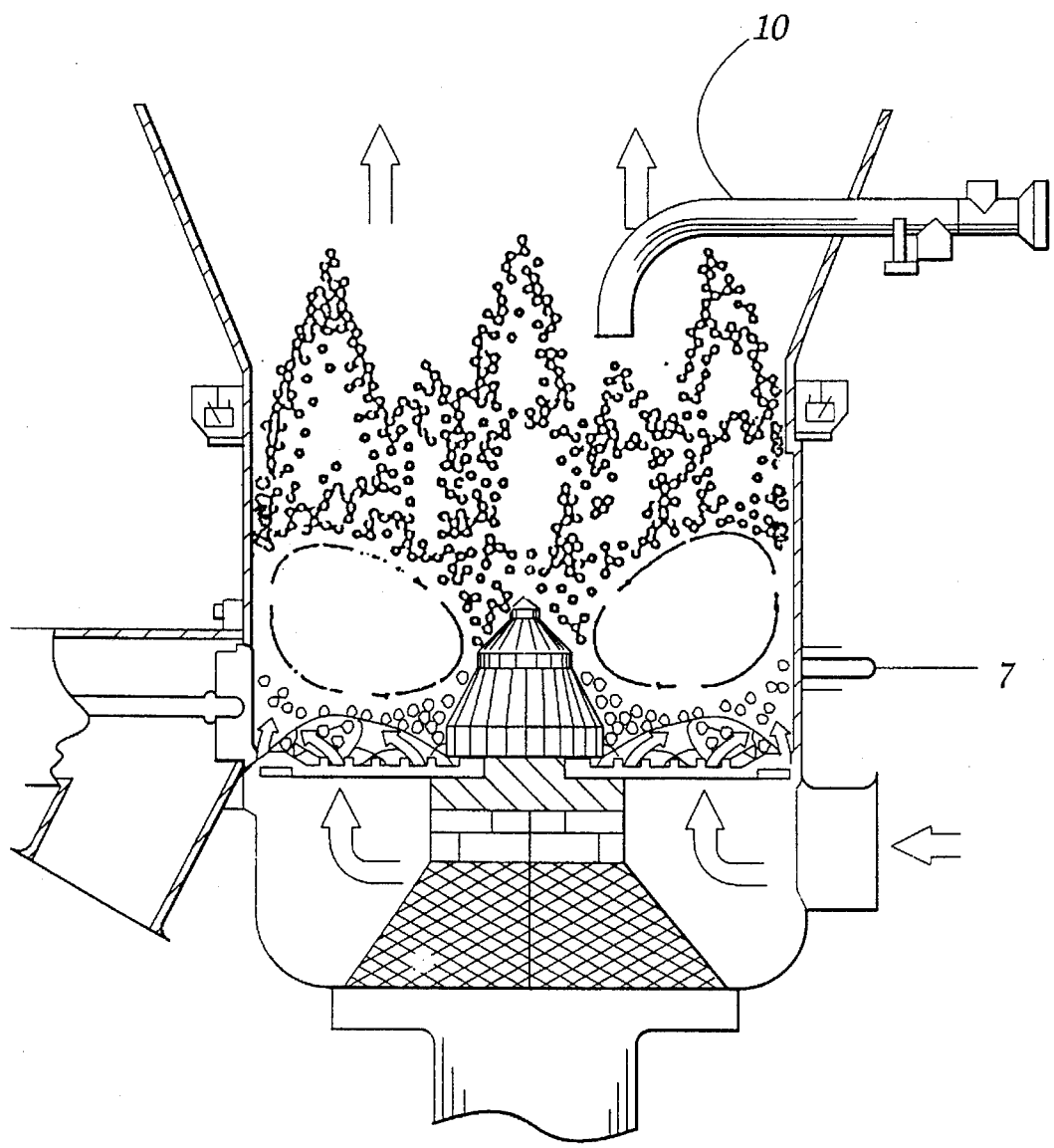
FIG. 6 is another cross-sectional view of a granulation/coating apparatus similar to FIG. 5 showing another embodiment of the photography probe of the present invention.
Figure 7:
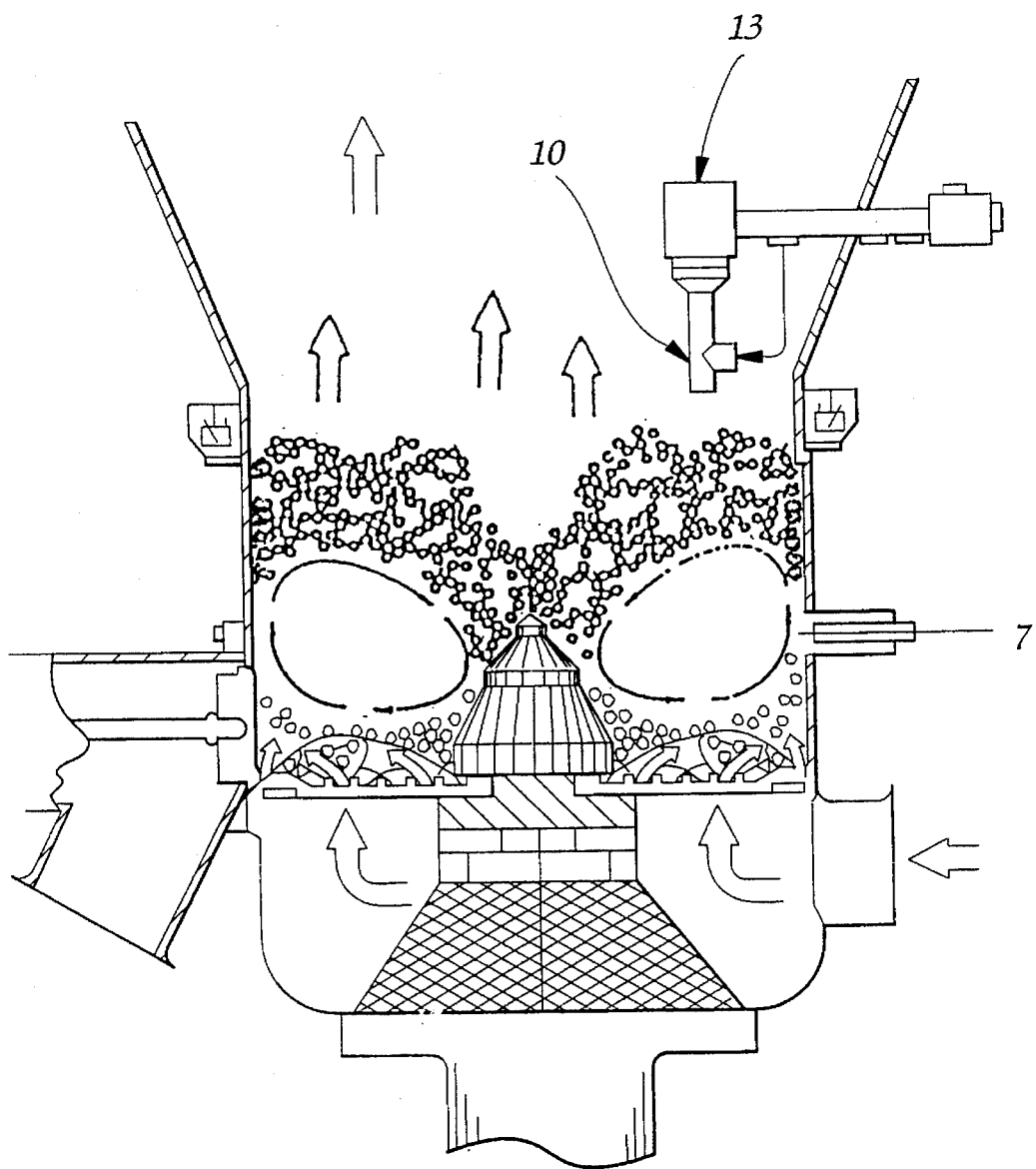
FIG. 7 is another cross-sectional view of a granulation/coating apparatus similar to FIGS. 5 and 6 showing another embodiment of the photography probe wherein a CCD camera is located in an upper portion of the granulation/coating chamber.
Figure 8:
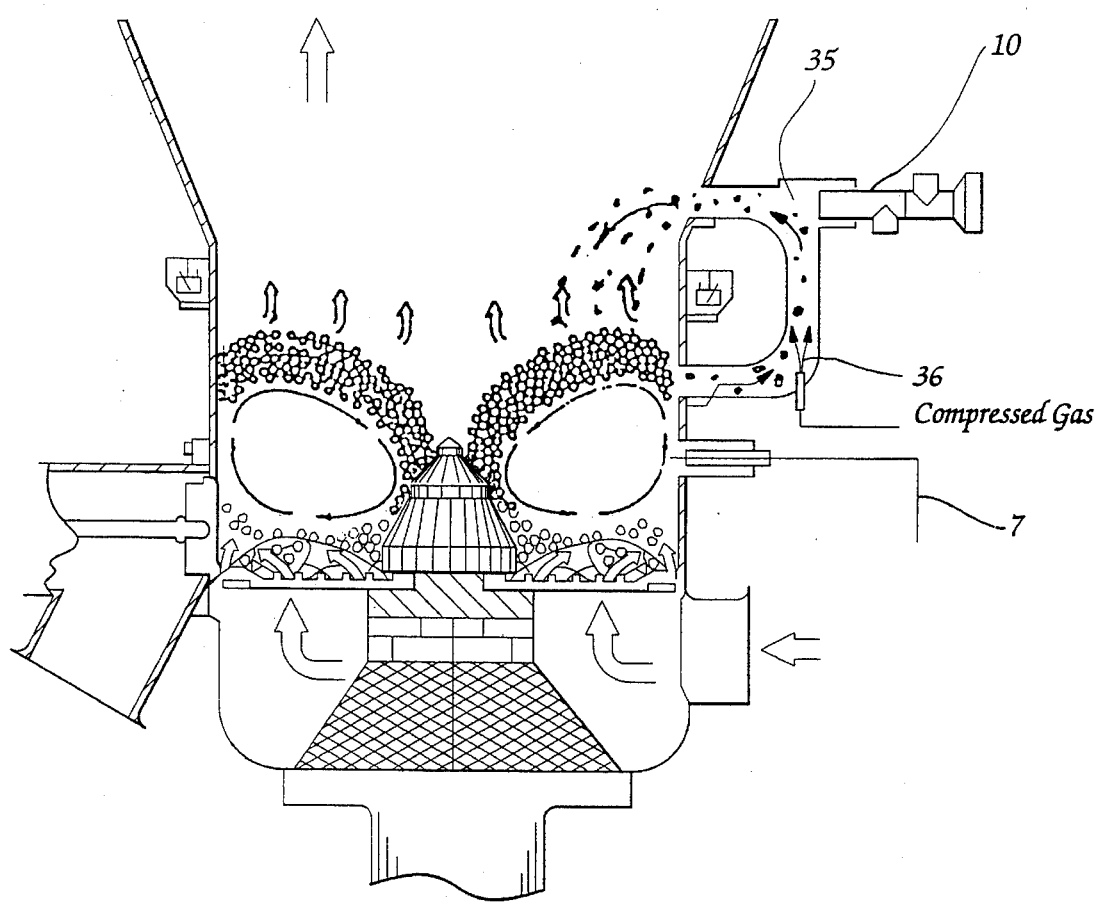
FIG. 8 is a cross-sectional view of a granulation/coating apparatus having an exteriorly-mounted guide passage through which the granular material is circulated with the aid of a gas injector.
Figure 9:
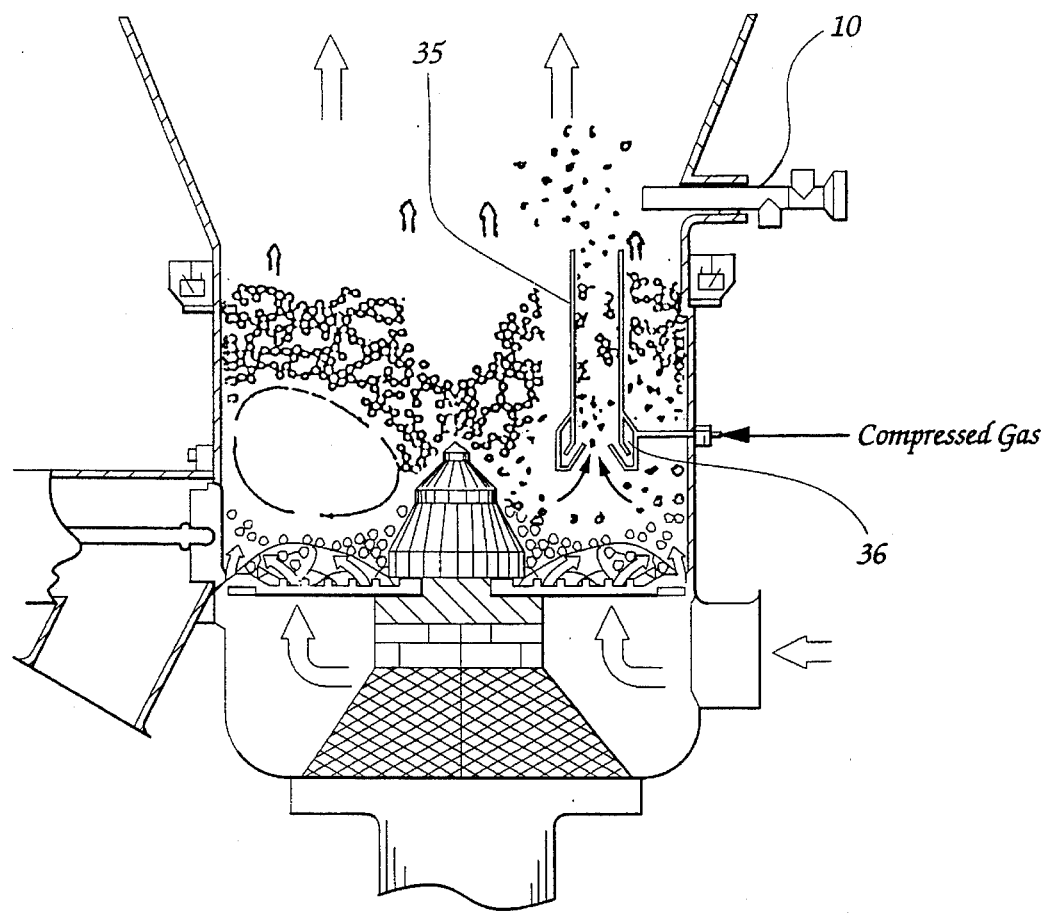
FIG. 9 is another cross-sectional view of a granulation/coating apparatus having a guide passage mounted in the granulation/coating chamber through which the granular material is circulated with the aid of a gas injector.
Figure 10:
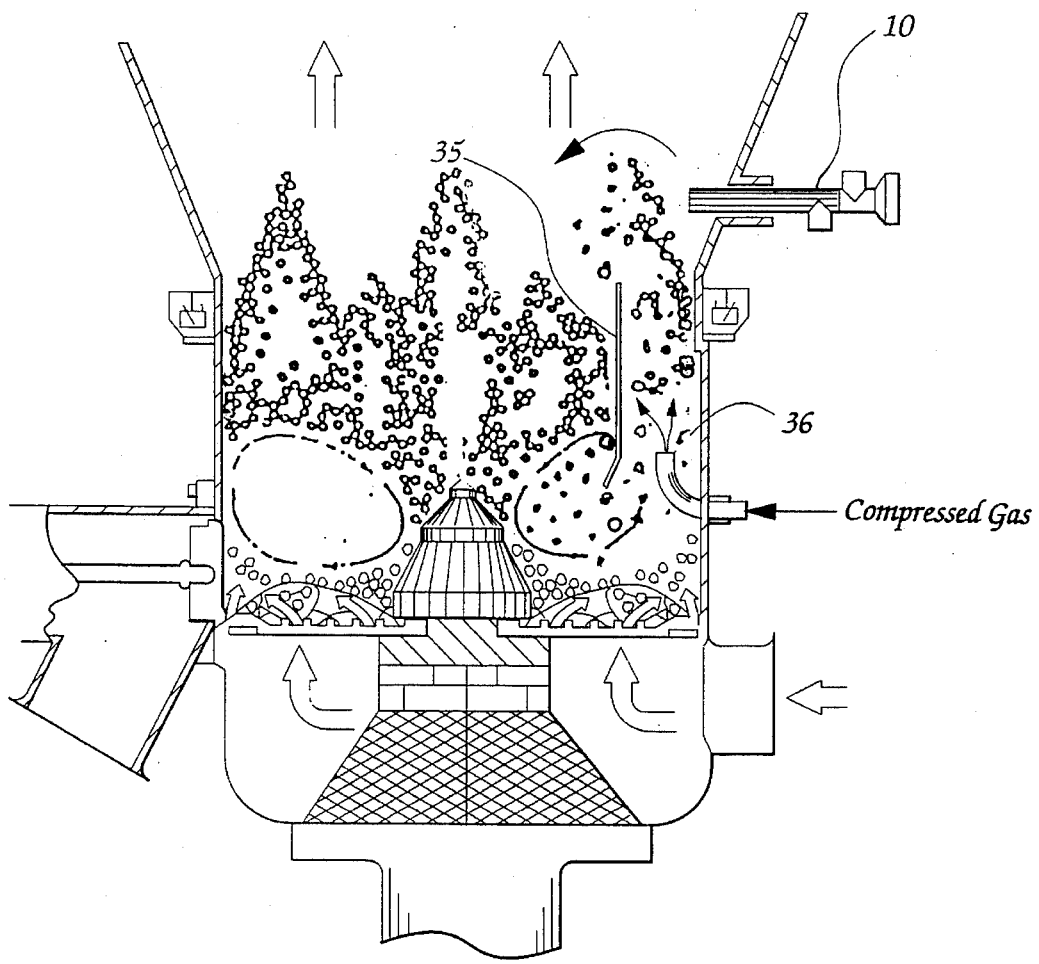
FIG. 10 is another cross-sectional view of a granulation/coating apparatus similar to FIG. 9 having a guide passage mounted in the granulation/coating chamber through which the granular material is lifted with the aid of a gas injector.

In the present invention, the distance by which granules are blown by the gas jet emitted from the terminal end opening 53 of the optical housing can be controlled by adjusting the gas flow rate or gas velocity and the degree of granule dispersion can also be controlled by adjusting the gas flow rate or gas velocity from each opening 47,53. Therefore, the optimal individualized dispersal of granules can be selectively positioned to occur within the planar projection of light from the opening 47 and the focal length of the photographic camera can be independently adjusted to coincide correspondingly in such plane. By way of example, FIG. 4 shows several photographs taken by the photography apparatus of the present invention during a granulation process, in which it will be seen that the granules are substantially dispersed and separated into individual particles and have clear contours in contrast to a dark background, suitable for further size and shape analysis by the image processor. The individual photographs represent sequential stages of granule growth over the course of the granulation process from an initial stage in FIG. 4A wherein the charge material is still in fine powder condition to a final stage in FIG. 4H wherein the granules have reached a desired size and shape.

As will thus be understood, the photography apparatus of the present invention advantageously enables the taking of still images of powder and/or granular material during a granulation or coating operation against a dark field or background. By means of the purge gas flow through the opening 53 disposed at the terminal end of the optical line, in combination with the intersecting purge gas flow through the slit-like opening 47 in the optical line, the powder and granular material disposed in the region of the intersecting gas streams is dispersed within the focal field of the optical line to obtain a clear and individualized image of the powder or granular material for analyzing its size and shape by the still-image processor during the granulation/coating process. Accordingly, the apparatus of the present invention can accomplish a real time monitoring of granule size and shape which enables a fully automated control of the granulation process and a consistent end product.

It is also possible to utilize the present photography apparatus for advanced granule quality control, i.e., a simultaneous granule size, shape and density control, by combination with another controlling system such as a granule moisture content monitoring system. For example, the granulating apparatus shown in FIG. 2 is equipped with a moisture content sensing device 7, which monitors and controls the moisture content of granules during granulation operation by adjusting the liquid feed rate from the spraying head for the binder or coating liquid, as well as adjusting the flow rate for the fluidizing gas through the gas supply conduit 4.

Conventionally, granule size, shape and density in the granulation chamber cannot be directly monitored during a granulation process, and granule size is mainly controlled by the moisture content of the granules on the assumption that granule size is dominated by its moisture content. Therefore, the termination point for stopping a granulating operation is determined by experimentally obtained data establishing an interrelation between mean granule size and its moisture content. Disadvantageously, this conventional control procedure sometimes results in poor process repeatability mainly due to fluctuation of operating parameters or conditions. Moreover, the interrelationship between processing time and granule shape can only be obtained by time-consuming development of experimental data.

More sophisticated granule quality control can be carried out under the present invention by following procedure. The particle size of powder raw material is monitored by the photography apparatus of this invention from the beginning of a granulation process. By spraying the binding liquid onto the powder raw material, the moistened powder material agglomerates gradually into granules. When the granule reaches a required or predetermined size, its moisture content is measured by the moisture content detector 7, and, thereafter, this prevailing moisture content level is kept constant by adjusting the liquid feed rate through the spray head 5, to control a moistening parameter of the operation, and the gas flow rate for fluidization through the conduit 4, to control a drying parameter of the operation. During this process, the granule size is maintained constant and its shape is monitored and analyzed by the present photography apparatus. Once the desired granule shape (i.e., its roundness or aspect ratio) is confirmed, the granulation process is terminated, whereby granules with the required shape and density (normally measured in terms of bulk density) are obtained.

Thus, the combination of the present invention with an existing monitoring system, such as an infrared moisture content sensor, enables a more sophisticated granulation process control. While this combined control system is described above by way of example with regard to the granulating and coating apparatus shown in FIG. 2, it is to be understood by persons skilled in the art that wider applications are contemplated in other types of apparatus such as fluidized-bed or tumbling-type granulators.

The apparatus of the present invention can also be applied to coating operations performed in fluid-bed coating apparatus, in which a coating liquid is normally sprayed onto seed particles, granules or other cores charged into the chamber of the apparatus. The coating liquid generally consists of film-forming materials such as polymers and diluting liquids such as water or organic solvents. When such a coating liquid is sprayed onto the seed particles, the water or solvent evaporates leaving a coated film on the individualized particles.

The apparatus of the present invention, when employed for a coating process, provides information during the process as to particle size distribution, film thickness, homogeneity of film quality, secondary agglomeration of seed particles (which deteriorates coating quality) and smoothness of the coated film. For example, information as to the thickness of the coated film is obtained by making a comparative analysis of the particle size distribution of the initially charged seed particles and that of the coated particles during the coating operation. Unfavorable secondary agglomeration, which takes place under conditions wherein the rate of moistening of the particles overcomes the rate of drying, is minimized or greatly reduced by monitoring the ratio of agglomerated particles to separated individual particles. When secondary agglomeration is found to be occurring, countermeasures can be immediately taken by increasing the gas flow rate through the conduit 4 to increase granule drying and/or the liquid feed rate through the nozzle may be decreased, depending upon the degree of secondary agglomeration detected.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. In a granulation or coating apparatus of the type having a processing vessel defining a granulation chamber for processing a particulate charge material therein into granules, an apparatus for photographing material under process in the granulation chamber for use in controlling physical characteristics of granules produced therein, the apparatus comprising means for projecting a source of illuminating light in the form of a generally flat beam through a portion of the granulation chamber, means for focusing a photographic camera within the projected light beam along an optical line of sight oriented generally perpendicular to the projected light beam, and means for directing a stream of gas in the region of the intersection of the projected light beam and the line of sight to disperse the charge material in the region during photography to promote photography of individualized particles of the charge material.

2. A granulation or coating apparatus according to claim 1 wherein the light projecting means comprises a bundle of optical fibers.

3. A granulation or coating apparatus according to claim 1 wherein the light projecting means and the camera focusing means are affixed together as parts of a unitary photographic probe inserted into the granulation chamber.

4. A granulation or coating apparatus according to claim 1 wherein the gas directing means is oriented to purge charge material from accumulating on the light projecting means and the camera focusing means.

5. A granulation or coating apparatus according to claim 4 wherein the gas directing means includes means for heating the gas.

6. A granulation or coating apparatus according to claim 1 wherein the gas directing means comprises means for directing a first stream of gas generally along the flat projected light beam and a second stream of gas generally along the optical line of sight.

7. A granulation or coating apparatus according to claim 6 wherein the gas directing means is arranged for discharging the first stream of gas annularly about the light projecting means and for discharging the second stream of gas annularly about the camera focusing means.

8. A granulation or coating apparatus according to claim 1 wherein the light projecting means comprises a stroboscope.

9. A granulation or coating apparatus according to claim 8 and further comprising control means for actuating the light projecting means and the camera focusing means in timed synchronism with one another.

10. In a granulation or coating apparatus of the type having a processing vessel defining a granulation chamber for processing a particulate charge material therein into granules, an apparatus for photographing material under process in the granulation chamber for use in controlling physical characteristics of granules produced therein, the apparatus comprising means for projecting a source of illuminating light through a portion of the granulation chamber, means for focusing a photographic camera within the projected light, and means for directing a stream of gas in the region of the light projecting means and the camera focusing means to purge charge material from accumulating thereon and to disperse the charge material in the region during photography to promote photography of individualized particles of the charge material.

11. A granulation or coating apparatus according to claim 10 wherein the light projecting means and the camera focusing means are affixed together as parts of a unitary photographic probe inserted into the granulation chamber.

12. A granulation or coating apparatus according to claim 10 wherein the light projecting means comprises a stroboscope.

13. A granulation or coating apparatus according to claim 10 wherein the gas directing means includes means for heating the gas.

14. A granulation or coating apparatus according to claim 13 wherein the gas directing means includes means for controlling the temperature of the heated gas to be generally constant.

15. A granulation or coating apparatus according to claim 10 and further comprising means for analyzing photographed images of the charge material in the granulation chamber with regard to size and shape of granules produced.

16. A granulation or coating apparatus according to claim 10 and further comprising means for sensing moisture content in charge material in the granulation chamber.

17. In a method of granulating or coating a particulate material into granules within a granulation chamber of a processing vessel, a method of controlling physical characteristics of the granules produced, the method comprising photographing the material under process in the chamber by projecting a source of illuminating light through a portion of the granulation chamber, focusing a photographic camera within the projected light, and directing a stream of gas in the region of the projected light and the camera focus to purge the material under process from accumulating on the light source or the camera and to disperse the process material in the region during photography to promote photography of individualized particles of the process material.

18. A granulating or coating method according to claim 17 and further comprising the step of analyzing photographed images of the process material in the granulation chamber with regard to size and shape of granules produced.

19. A granulating or coating method according to claim 17 and further comprising the steps of measuring the moisture content of the process material when the photographing step indicates that a predetermined mean granule size is achieved, maintaining the moisture content of the material generally constant at the measured value while continuing granulating operation within the chamber, and terminating the granulating operation when the photographing step indicates a predetermined granule shape has been achieved.

20. A granulating or coating method according to claim 17 and further comprising the steps of measuring the moisture content of the process material when the photographing step indicates that a predetermined mean granule size is achieved, maintaining the moisture content of the material generally constant at the measured value while continuing granulating operation within the chamber, and terminating the granulating operation when the photographing step indicates a predetermined distribution of granule sizes has been achieved.

* * * * *